United States Patent [19]

Hayhurst et al.

[11] Patent Number: 5,224,946
[45] Date of Patent: * Jul. 6, 1993

[54] BONE ANCHOR AND METHOD OF ANCHORING A SUTURE TO A BONE

[75] Inventors: John O. Hayhurst, Milwaukie, Oreg.; Alan A. Small, Needham, Mass.; Jeffrey C. Cerier, Franklin, Mass.; Paul DiCarlo, East Falmouth, Mass.; James W. Dwyer, Brookfield, Conn.

[73] Assignee: American Cyanamid Company, Stamford, Conn.

[*] Notice: The portion of the term of this patent subsequent to Aug. 6, 2008 has been disclaimed.

[21] Appl. No.: 681,070

[22] Filed: Apr. 5, 1991

Related U.S. Application Data

[63] Continuation-in-part of Ser. No. 547,783, Jul. 2, 1990, Pat. No. 5,037,422.

[51] Int. Cl.$^5$ ............................................. A61B 17/00
[52] U.S. Cl. ..................................... 606/72; 606/74; 606/75; 606/232; 606/144
[58] Field of Search ................ 128/899; 606/144, 220, 606/72-75, 232

[56] References Cited

U.S. PATENT DOCUMENTS

| | | | |
|---|---|---|---|
| 3,845,772 | 11/1974 | Smith | 128/335 |
| 4,013,071 | 3/1977 | Rosenberg | 606/73 |
| 4,275,717 | 6/1981 | Bolesky | 128/92 |
| 4,409,974 | 10/1983 | Freedland | 606/232 |
| 4,454,875 | 6/1984 | Pratt et al. | 128/92 |
| 4,476,861 | 10/1984 | Dimakos et al. | 128/303 |
| 4,532,926 | 8/1985 | O'Holla | 128/334 |
| 4,653,486 | 3/1987 | Coker | 128/92 |
| 4,738,255 | 4/1988 | Goble et al. | 606/232 |
| 4,772,286 | 9/1988 | Goble et al. | 623/13 |
| 4,776,328 | 10/1988 | Frey et al. | 128/92 |
| 4,946,468 | 8/1990 | Li | 606/232 |
| 5,046,513 | 9/1991 | Gattarna et al. | 606/72 |
| 5,100,417 | 3/1992 | Cerier et al. | 606/139 |

FOREIGN PATENT DOCUMENTS

0260970 3/1988 European Pat. Off.
2606270 5/1988 France.
WO89/10096 11/1989 PCT Int'l Appl.

OTHER PUBLICATIONS

Russell Warren, M.D., Technique for Using the TAG Tissue Anchor-Rod Style, Published Jul. 16, 1990.
John O. Hayhurst, M.D., Technique for Using the TAG Tissue Anchor-Wedge Style, Published Jul. 16, 1990.
Arthrex Brochure-"Arthrex ESP System: Expanding Suture Plug", Feb. 1991, [Published prior to Mar. 1, 1991].

Primary Examiner—Stephen C. Pellegrino
Assistant Examiner—Gary Jackson
Attorney, Agent, or Firm—Douglas E. Denninger

[57] ABSTRACT

A bone anchor (10) for securing a suture to a bone (38). The bone anchor (10) has a tip (16) at its distal end (18) and at least one resilient wall (27) extending to a trailing end (20) of the body (12) of the anchor. The wall (27) has a ridge (14), or barb, formed on an outer surface. The ridge (14) defines an edge (34) that digs into a hole (36) in the bone (38) in which it is positioned. A strand of suturing thread (22) extends through a suture receiving opening (24) in the tip (16) of the anchor. The method of the present invention employs the suture anchor (10) and includes the steps of forming a hole (36) in a bone (38) and inserting the suture anchor (10) to a desired depth in the hole (36) in the bone (38) using an inserter device (100). Suturing thread (22) extends from the suture receiving opening (24) in the tip and along the length of the walls (27,28) out of the hole (36) in the bone (38). An anchor spreader (130) is used to firmly seat the anchor (10) in the hole (36). The suture (22) is pulled at the same time to help seat the barbs 14 on the anchor (10) into the bone (38).

12 Claims, 3 Drawing Sheets

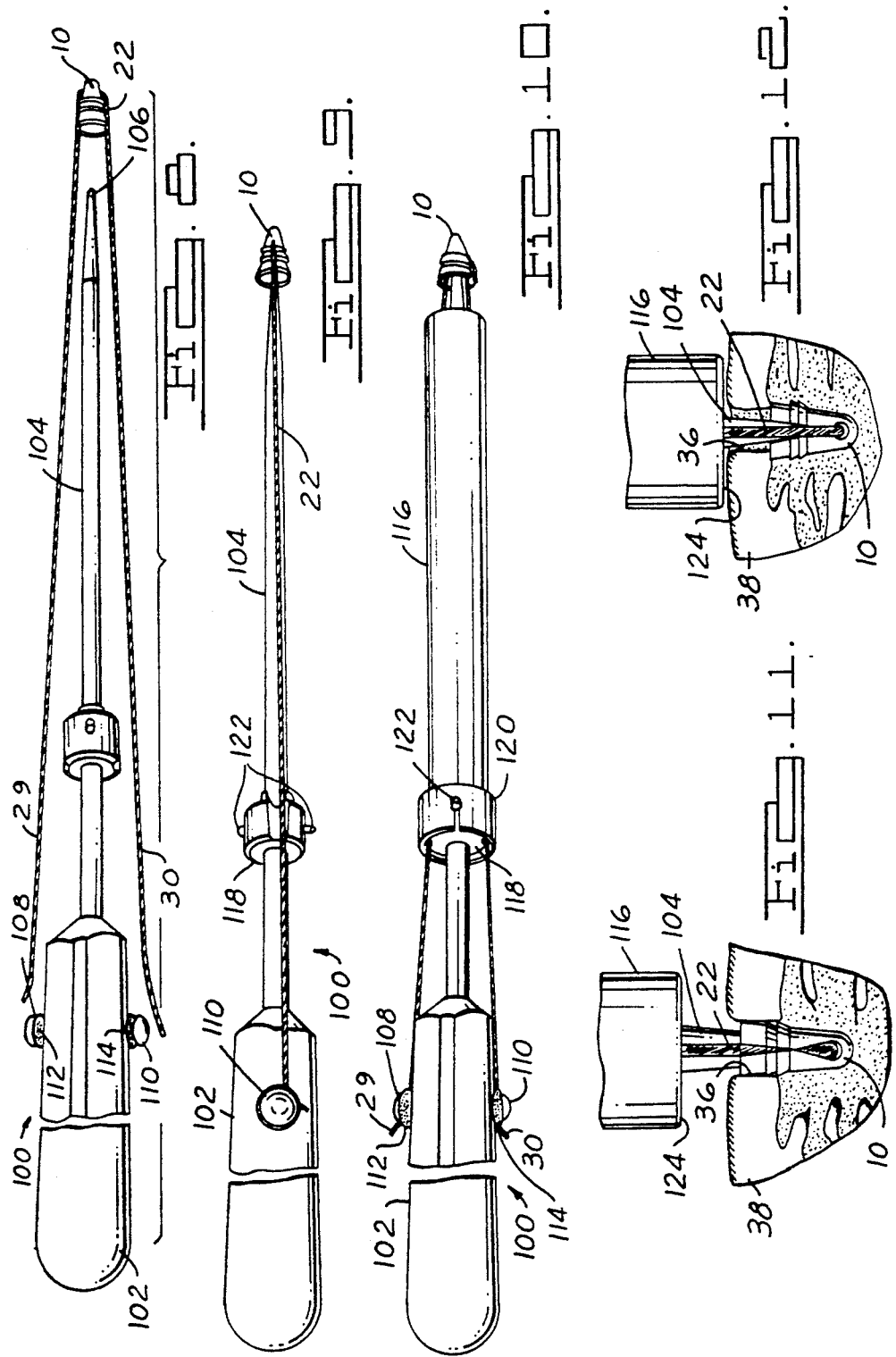

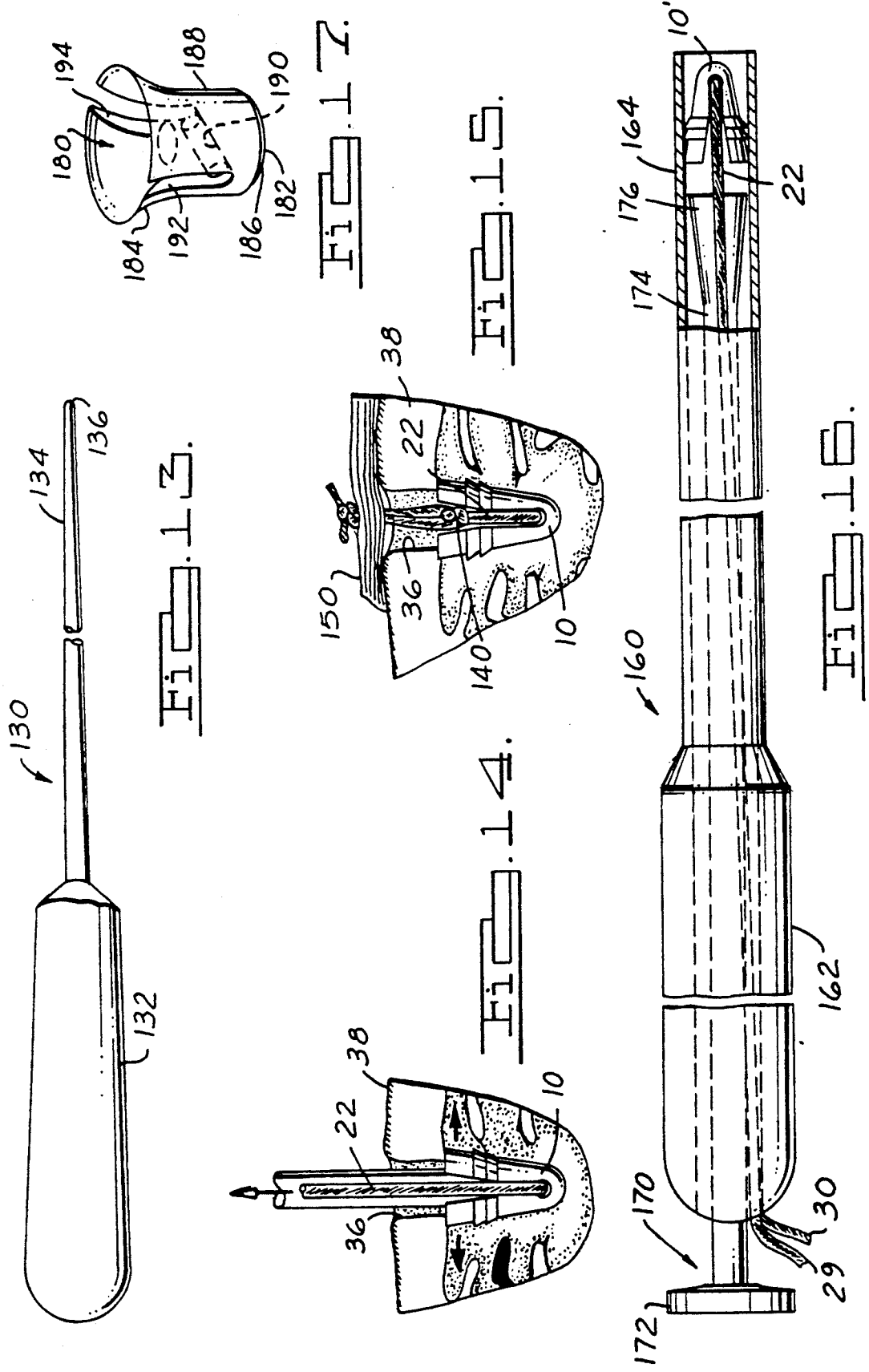

BONE ANCHOR AND METHOD OF ANCHORING A SUTURE TO A BONE

CROSS REFERENCE TO RELATED APPLICATIONS

This is a continuation-in-part of commonly owned patent application Ser. No. 547,783, filed Jul. 2, 1990 now U.S. Pat. No. 5,037,422.

TECHNICAL FIELD

The present invention relates to anchors for surgical sutures, and more particularly relates to bone anchors which are inserted into a hole formed in a bone.

BACKGROUND ART

Suture anchors used to secure sutures in openings formed in bones are important for joint reconstructive surgery and arthroscopic surgical techniques. Such suture anchors are used, for instance, to anchor ligaments or tendons to bones in knee, shoulder and elbow reconstruction and repair operations.

Important attributes of bone anchors are that they be easy to insert, and provide a firm anchor. Bone anchors also should be simple and reliable. Bone anchors may be bio-absorbable or nonbio-absorbable depending upon the material used to form the bone anchor. Either can be used depending on the type of operation and selection of the surgeon.

Initially, one type of bone anchor took the form of a fish hook-type barb which was inserted into a hole and hooked into the soft marrow of the bone. Another prior approach to suture anchors is disclosed in Goble et al. U.S. Pat. No. 4,738,255. This patent discloses a suture anchor delivery system which uses a specialized two-piece anchor including an anchor rivet and a slotted ring. The anchor rivet is drawn into the slotted ring to deform the slotted ring into an acorn-shape when pressure is applied by an anchor mandrel through which the suture is drawn. This slotted ring includes slots that are split to allow the ring to be deformed and an anchor ridge is formed around the inside circumference of the slotted ring. As compared with the present invention, the Goble suture anchor is more complex in configuration and requires a specialized anchor delivery system for manipulating the two-piece rivet and slotted ring. Also, manufacture of the Goble suture anchor requires close tolerance assembly of the two-piece anchor and cooperation between the two parts of the anchor.

Another patent disclosing a system for fastening articles to bones is disclosed in Rosenberg U.S. Pat. No. 4,013,071. This patent discloses an orthopedic screw with an expandable portion including side slits which are formed radially through the distal end of a screw. The side slits produce a plurality of outwardly expansible tips that are flared by driving a rod-shape member through an internal bore of the orthopedic screw. The Rosenberg device is turned in a manner of a screw for insertion which presents some difficulties in performing arthroscopic procedures. Further, the Rosenberg device requires close tolerance in manufacturing and assembly.

Still another prior art system is shown in Hayhurst U.S. Pat. No. 4,741,330. This patent discloses anchoring devices for attaching sutures to bones, the anchoring devices being deformable cylindrical shaped solid plugs attached at their midpoints to sutures.

A primary objective of the present invention is to provide a bone anchor which is inexpensive to manufacture and simple to install.

Another object of the invention is to provide a bone anchor which automatically locks itself into a bore formed in a bone by simply applying pressure to the suture which causes the barbs or ridges in the bone anchor to dig into the walls of the hole in the bone locking the anchor to the bore hole.

Still another aspect of the present invention is to provide a bone anchor which is compact and automatically guides itself into the hole in the bone.

Another important object of the invention is to provide a bone anchor which may be formed by a simple molding operation with no close tolerance assembly operations required. This feature makes the bone anchor both economical and reliable.

A further object of the invention is to provide an inserter device for installing the bone anchor in place, as well as a spreader device for helping to firmly seat the anchor in the bone.

These and other objects are met by the present invention which will become apparent upon review of the following detailed description of the invention in view of the drawings.

DISCLOSURE OF INVENTION

The present invention relates to a bone anchor intended to be used with a suture to secure the suture to a hole formed in a bone. The bone anchor is an elongated thimble-shaped body having a tip at one end of the body. First and second slots extend lengthwise through the elongated body at spaced locations. A suture receiving opening is provided in the tip. At least one ridge, or barb, extends outwardly from the exterior of the elongated body and defines an edge which is adapted to be lodged in the wall of the bore formed in the bone. In one embodiment, a sharp trailing edge comprises the ridge.

The tip of the anchor is its leading end as it is inserted into the bore hole in the bone, and is preferably partially conical in shape and terminates in a rounded end. The conical tip has a rounded end that aides in aligning the anchor with the bore hole in the bone. First and second slots are preferably formed in a substantially cylindrical portion of the anchor and are preferably diametrically opposed. The suture receiving opening in a preferred embodiment extends from the side of the body in which the first slot is formed to the side of the body in which the second slot is formed. The suture is threaded through the suture receiving opening and rearwardly relative to the anchor through the first and second slots and out of the bore hole. A suture trails behind the anchor and out of the bore in the bone so that it is accessible for surgical suturing.

The bone anchor is installed in the bone by means of an inserter device and a spreader device. The inserter device has an elongated shaft attached to a handle member. In the preferred embodiment, the anchor is positioned on the end of the shaft and held in place by the sutures which are attached to posts on the handle. In another embodiment, the inserter device is hollow and the anchor is pushed through it and inserted in the bone by a pusher member. Once the anchor is installed in place, an elongated anchor spreader is used to firmly seat it in position.

BRIEF DESCRIPTION OF DRAWINGS

FIGS. 8 and 9 show the use of the inventive anchor with an inserter device;

FIG. 10 shows the use of a depth member with the inserter device;

FIGS. 11 and 12 illustrate the installation of the anchor using an inserter device with a depth member;

FIG. 13 shows a spreader device for use with the present invention;

FIG. 14 illustrates the use of a spreader device;

FIG. 15 illustrates one anticipated use of the present invention;

FIG. 16 illustrates an alternate embodiment of the invention; and

FIG. 17 depicts still another embodiment of the bone anchor.

BEST MODE(S) FOR CARRYING OUT THE INVENTION

Figure 1:
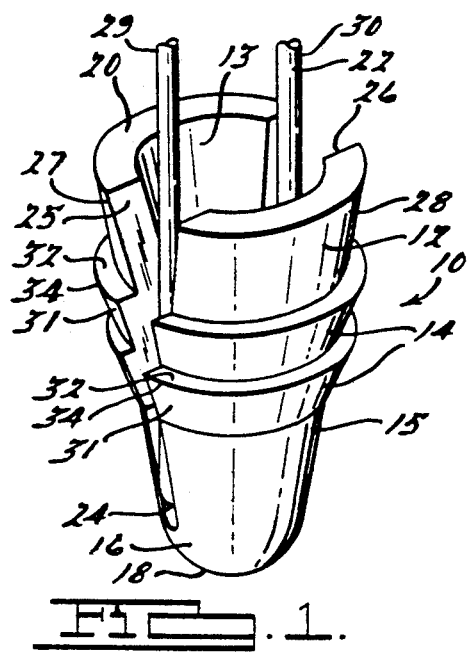
FIG. 1 is a perspective view of a bone anchor made in accordance with the present invention.
Figure 2:
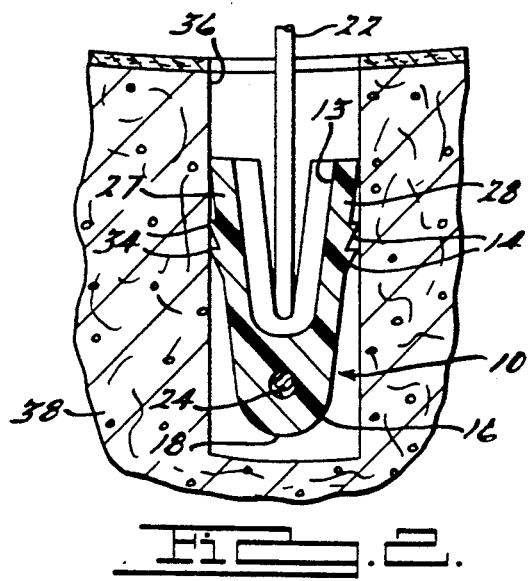
FIG. 2 is a cross-sectional view showing the bone anchor of the present invention inserted in a hole formed in a bone.
Figure 3:
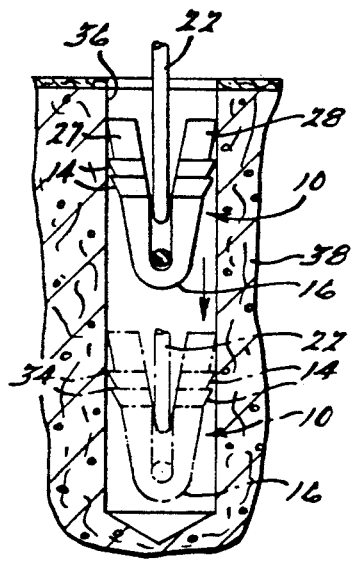
FIG. 3 is a cross-sectional view showing a bone anchor being inserted and then locked into a hole in the bone.

Referring now to FIG. 1, the bone anchor of the present invention is generally indicated by reference numeral 10. The bone anchor 10 includes a thimble-shaped body 12 which defines an inner cavity 13. A ridge 14, or barb, is formed on the outer surface 15 of the body 12. The ridge is preferably a circular ridge extending about the circumference of the body 12. A tip 16 is formed on the distal end 18 of the body 12. A trailing end 20 of the body 12 is located at the opposite end of the body from the distal end 18. A strand of suture filament 22, or suturing thread, is connected to the body 12 and preferably extends through a suture receiving opening 24 formed through the tip 16 of the body 12.

First and second slots 25 and 26 extend longitudinally through the body 12 from the tip 16 through to the trailing end 20. First and second slots 25 and 26 divide the body 12 into first and second resilient walls 27 and 28. First and second walls 27 and 28 are spaced from each by the first and second slots 25 and 26 and the inner cavity 13. The strand of suture filament 22 extends from the suture receiving opening 24 and is doubled back so that first and second lengths 29 and 30 of the strand extend from the tip 16 through first and second slots 25 and 26, respectively, and extend past the trailing end 20 for use by the surgeon. The first and second lengths of strand 29 and 30 are recessed in the first and second slots 25 and 26 so that the strands do not interfere with the locking action of the ridge 14.

The ridge 14 may be formed as a semi-circular circumferentially extending member. The ridge includes a frustoconical leading surface 31 and a radially extending back surface 32 which intersect to form a relatively sharp edge 34 at the outermost point on the ridge 14. The back surface 32 may be inclined to provide a sharper edge to enhance the ability of the bone anchor 10 to grip the sides of the bore hole 36 in a bone 38.

Referring now to FIGS. 2 through 5, insertion of the bone anchor will be described in greater detail. The bone anchor 10 is inserted into the bore hole 36 formed in the bone 38 by known rotary cutting implements. The tip 16 of the body 12 is preferably rounded and tapered so that it centers itself radially relative to the bore hole 36. As the bone anchor is pushed into the bore hole 36, first and second walls 27 and 28 resiliently converge. The ridge 14 formed on the body 12 preferably has a normal diameter greater than the diameter of the bore hole 36 so that an interference fit is established if the first and second walls 27 and 28 are not pushed together. The bone anchor 10 is pushed into the bore hole 36 by a rigid probe or a specialized insertion tool. When the bone anchor 10 is inserted to the proper depth in the bore hole 36, tension may be applied to the first and second lengths 29 and 30 of the strand 22. Upon application of tension, the edge 34 moves into the sides of the bore hole 36 and grips the bore hole. This causes the first and second resilient walls 27 and 28 to expand outwardly firmly locking the bone anchor in place.

Figure 4:
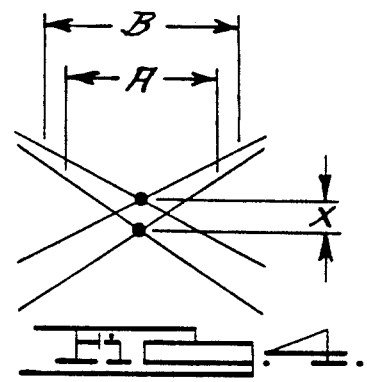
FIG. 4 is a schematic representation showing the scissoring action of the bone anchor when tension is applied after insertion.
Figure 5:
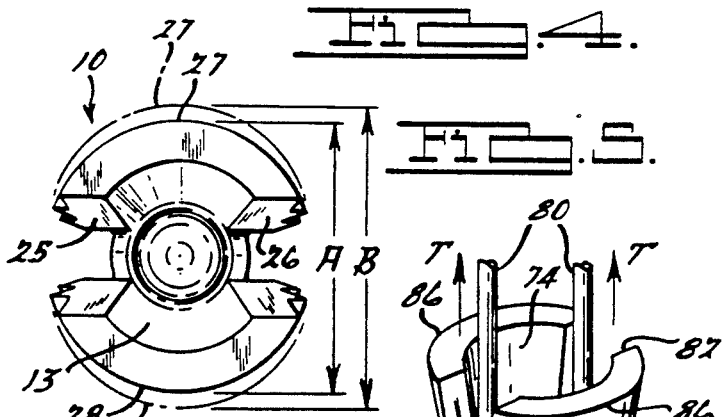
FIG. 5 a top plan view showing the bone anchor of the present invention and showing the bone anchor expanded in phantom.

As shown schematically in FIG. 4, when tension is applied to the strand 22, the suture receiving opening 24 shown diagrammatically is displaced upwardly a distance X. This upward movement causes the edges 34 to scissor outwardly from an insertion position at a diameter A to an installed position shown by diameter B. Expansion of the bone anchor is shown in FIG. 5 in a top plan view with the bone anchor expanding from a diameter A to a diameter B. Diameter A corresponds to the compressed dimension of the bone anchor while diameter B corresponds to the outwardly scissored dimension or expanded dimension.

The suture receiving opening 24 preferably extends in a line parallel to a line extending through the first and second slots 25 and 26. In this way, the first and second lengths 29 and 30 of the strand 22 may be simply routed from the ends of the suture receiving opening 24 through the first and second slots 25 and 26.

Figure 6:
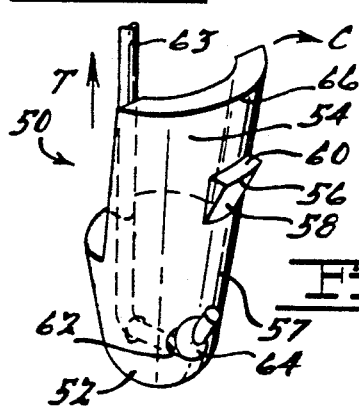
FIG. 6 is a perspective view of an alternative embodiment of the bone anchor of the present invention.

Referring now to FIG. 6, an alternative embodiment of the present invention is generally referred to by reference numeral 50. The bone anchor 50 includes a tip 52 and an arcuate wall 54 which extends rearwardly from the tip 52. A barb 56 is shown on the outer surface 57 of the arcuate wall 54. The barb 56 is formed by a leading ramp surface 58 and a rear facing surface 60. The sharpness of the barb may be varied by changing the angle of the rear facing surface 60. The tip 52 has a suture receiving opening 62. The suture receiving opening 62 is preferably connected to the tip 52 by a knot 64. The suture receiving opening 62 preferably extends from a point below the arcuate wall 54 on the tip 52. The suture receiving opening extends through the tip 52 and rearwardly from the tip. A trailing edge 66 is formed on the opposite end of the bone anchor 50 from the tip. The trailing edge 66 may perform the function of the barb 56 in that it may define an edge that can grip the sides of a bore hole in a bone upon application of tension designated by the letter T on the suture strand 63. When tension T is applied to the suture strand 63, the bone anchor 50 is tipped, or partially rotated, to cause the barb 56 to become lodged in the side of the bore hole. If the barb 56 is not provided, the trailing edge 66 would rotate and could form the anchoring edge in place of the barb 56. The tipping or partial rotation of the bone anchor 50 is shown by arrow C and occurs when tension is applied as denoted by arrow T.

Figure 7:
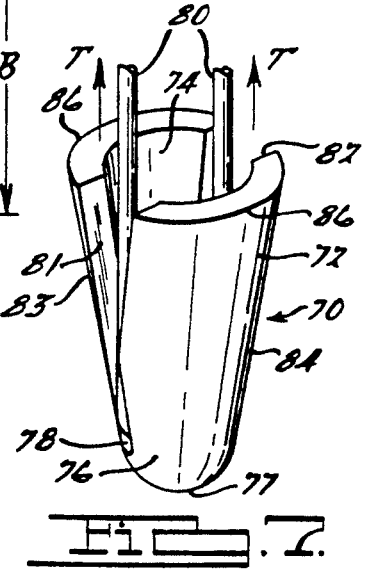
FIG. 7 is a perspective view of another alternative embodiment of the bone anchor of the present invention.

Referring now to FIG. 7, another alternative embodiment of the present invention is generally indicated by reference numeral 70. The bone anchor 70 includes a thimble-shaped body 72 which defines an inner cavity 74. The thimble-shaped body 72 has a tip 76 at its distal end 77. A suture receiving opening 78 extends through the tip 76 to form a passageway through the tip. A strand, or thread, of suture material 80 is threaded through the suture receiving opening 78 and is doubled back through first and second slots 81 and 82. First and second slots 81 and 82 divide the body 72 into first and second resilient walls 83 and 84. The suture material 80 is routed through the first slot 81, then through the suture receiving opening 78 and back through the second slot 82. Both ends of the thread of suture material 80 extend out of the bore hole in a bone when the bone anchor 70 is inserted therein. A relatively sharp trailing edge 86 of the body 72 is located at the opposite end of the body 72 from the distal end 77. The trailing edge 86 forms the barb or ridge that engages the sides of the bore hole. When tension, designated by letter T, is applied to both ends of the thread 80, the trailing edge 86 of the first and second walls 83 and 84 dig into the sides of the bore hole in the bone and are allowed to expand outwardly away from each other to cause the bone anchor 70 to become lodged in the bore hole.

The material used to form the bone anchor may be made of either a bio-absorbable material or a non-absorbable permanent material. Preferred absorbable materials include polyglycolic acid, polylactic acid or trimethylene carbonate copolymers. Preferred non-absorbable materials include acetal homopolymers or copolymers, polyethylene, polypropylene, polyester and copolymers thereof. Delrin 150 SA is one preferred material for the bone anchor. The suture material may be any conventional type of suture material, such as Ticron, or Dexon brand sutures which are trademarks of Davis & Geck.

An inserter device 100 for use with the inventive bone anchor 10 is shown in FIG. 8. The device 100 has a handle member 102 and an elongated shaft 104. The shaft 104 has a tapered end 106 which is conformed to fit into the inner cavity 13 of the anchor.

When the anchor 10 is positioned on the end 106 of the shaft 104, the two ends 29, 30 of the suture 22 are securely tightened around posts 108 and 110 on the handle 102. Rubber 0-rings 112 and 114 positioned under the heads of the posts 108 and 110 retain the sutures tightly in position after they are wrapped around the posts. The completed assembly of the bone anchor and the inserter device is shown in FIG. 9.

FIG. 10 illustrates the anchor and inserter assembly with a depth member or tube 116 positioned on it. The depth member 116 is positioned over the end of the elongated shaft 104 and held in place on stop or collar member 118 which is soldered to the shaft. The depth member 116 is made from a plastic material (such as Delrin grade 550) and has a pair of slots 120 which snap over pins 122 on the stop member in order to hold it in place on the inserter device.

The end 124 of the depth member 116, as shown in FIGS. 11 and 12, limits the insertion movement of the inserter 100 and thus limits the depth to which the bone anchor can be positioned in the bone 38. This ensures that the anchor will not be inserted too deeply. The depth member also protects the sutures during use of the driver and anchor assembly. The depth member 116 can be provided in different lengths in order to provide the insertion depth of the anchor below the cortical surface as desired by the surgeon.

The insertion of the bone anchor 10 can be accomplished with direct pressure, although the preferred and more controlled manner is to gently tap the end of the inserter device 100 with a small mallet advancing the anchor slowly. Once past the cortical bone, and without a depth member or device of some type, too much pressure could drive the anchor too deeply into the cancellous bone.

Once the anchor 10 is positioned in place, as shown in FIG. 12, the inserter device 100 is removed. A spreader device 130 is then used to firmly set and seat the anchor. As shown in FIG. 13, the device 130 has a handle 132 and a probe 134. The probe 134 has a rounded slightly tapered end 136 and is larger in diameter than the elongated shaft 104 on the inserter device.

In order to set the anchor 10, the spreader 130 is placed in the center of the anchor 10 (see FIG. 14) and the two ends of the suture 22 are pulled at the same time. This assists in opening the walls 27, 28 firmly seating the anchor in the bone.

When setting the anchor 10, it is important to firmly hold or clamp both ends of the suture so that it will not pull out of the anchor. One option at this point is to tie the two suture ends together, making sure the knot 140 (FIG. 15) is below the bone surface.

Once the anchor is installed and seated in place, the ligament 150 or other soft tissue is brought into position over the anchor site. The suture is then knotted firmly through the ligament holding it tightly in place next to the bone. This is shown in FIG. 15. In this manner, the soft tissue and bone will, over time, reattach themselves together.

Another embodiment of the invention is shown in FIG. 16. In this embodiment, the anchor 10' with suture 22 attached is inserted through a hollow insertion device 160. The device 160 has a handle 162 and insertion tube 164 and the bone anchors 10' are sized to slidingly fit within the tube. The anchors 10' are installed in position by a pusher member 170 which has a head or handle 172 and elongated pusher rod 174. The end 176 of the pusher rod can be pointed to fit within the center cavity of the anchor 10' (similar to the end 106 of inserted device 100), or, as shown, can be flattened or enlarged.

The "hollow tube" insertion method is particularly useful for small anchors, on the order of about one-sixteenth of an inch in diameter and three-sixteenths of an inch in length. Also, in order to gauge and measure the depth of insertion of the anchor 10', markings or a scale (not shown) can be provided on the pusher rod 174 adjacent the head or handle.

Once the bone anchor 10' is inserted in the opening or bore 36 in the bone 38, a spreader device (similar to spreader 130 described above) is used to firmly seat the anchor in place. Thereafter, the anchor can be used inthe same manner and for the same purposes as described above with respect to anchor 10.

Another embodiment of the bone anchor is shown in FIG. 17. The bone anchor 180 has a relatively flat front end 182 and an outwardly flared ridge 184 on its rear end. The front end 182 has a 45° chamfer 186 in order to aid in entry of the anchor into the drilled hole in the bone. The rear end has a recess 188 which allows the outwardly flared annular ridge 184 to be flexible and move radially inwardly during insertion. The "memory" of the anchor material, together with expansion by a spreader member, forces the ridge 184 outwardly securely holding the anchor in position. An opening 190 and opposed slots 192, 194 are provided through the anchor for a suture.

The preceding description of the preferred embodiments of the present invention is intended to be illustrative of three preferred forms of the invention. It is anticipated that other modifications and enhancements of the present invention will be apparent based upon the above description. The scope of the present invention should be measured by the following claims, and not limited by the above description of the preferred embodiments.

We claim:

1. A method of anchoring a suture in a bone with a suture anchor having a tip on a leading end, said tip including a hole through which a length of suturing thread extends, at least one resilient wall forming a trailing portion of the suture anchor, said wall having a barb formed on an outer surface which faces a wall of the hole in the bone, said barb defining an edge which is adapted to engage the wall of the hole in the bone, comprising the steps of:

forming a hole in the bone;
   inserting said suture anchor to a desired depth in the hole in the bone with the tip being inserted first, the trailing portion following said tip, and the suturing thread extending from the hole in the tip and then along the length of said trailing portion and out of the hole in the bone;
   pulling on the portion of the suturing thread extending out of the hole and thereby urging the barb into firmer engagement with the wall of the hole in the bone; and
   urging said resilient wall of said body against the bone in the hole by a spreader member.

2. A method of anchoring a suture in a bone with a suture anchor having a tip on a leading end, said tip including a hole through which a length of suturing thread extends, at least one resilient wall forming a trailing portion of the suture anchor, comprising the steps of:

forming a hole in the bone;
   inserting said suture anchor to a desired depth in the hole in the bone with the tip being inserted first, the trailing portion following said tip, and the suturing thread extending from the hole in the tip and then along the length of said trailing portion and out of the hole in the bone; and
   urging said resilient wall of said body against the bone in the hole by a spreader member.

3. A method of anchoring a suture in a bone with a suture anchor having a tip on a leading end, the tip including a hole through which a length of suturing thread extends, at least one wall forming a trailing portion of the body, the wall having a barb defining an edge which is adapted to engage the wall of the hole in the bone, comprising:

forming a hole in the bone;
   predetermining a desired depth of insertion by selecting an inserter device having a handle and a depth member, spaced distal to the handle, for limiting insertion to the desired depth of insertion of the suture anchor in the hole;
   inserting the suture anchor with the inserter device to the desired depth in the hole in the bone with the tip being inserted first, the trailing portion following the tip, and the suturing thread extending from the hole in the tip and then along the length of said trailing portion and out of the hole in the bone; and
   pulling on the portion of the suturing thread extending out of the hole and thereby urging the barb into firmer engagement with the wall of the hole in the bone.

4. The method of claim 3 in which the depth member is removable from the remainder of the insertion device and further including mounting the removable depth member on the inserter device after the suture anchor is positioned on the inserter device.

5. A bone anchor for securing a suture to a bore hole in a bone in combination with a pusher member and a depth member, the combination comprising:

a bone anchor including an elongated body having a tip at a distal end of the body and means for carrying a suture;
   a pusher member having a handle and a distal tip engagable with said body; and
   a depth member being removably disposed on said pusher member distal to the handle to control the depth to which said body is inserted within the hole in the bone.

6. The combination of claim 5 in which the depth member is a hollow sleeve having a proximal end for engaging a stop member carried by the inserter device, and having a distal end with an end face defining a distal opening through which the suture anchor protrudes after assembly.

7. The combination of claim 6 in which the sleeve is cylindrical.

8. The combination of claim 5 in which the bone anchor further includes at least one ridge extending outwardly from the exterior of the body and defining an edge adapted to lodge in the wall of the bore hole.

9. The combination of claim 5 in which said bone anchor includes at least two resilient walls which define between them first and second slots, said walls being compressible toward each other when the bone anchor is inserted into the hole in the bone, said first and second slots extending lengthwise at spaced locations on the body, and said means for carrying including a suture receiving opening extending through the tip.

10. The combination of claim 5 in which said bone anchor includes at least two resilient walls which define between them first and second slots, said walls being compressible toward each other when the bone anchor is inserted into the hole in the bone, said first and second slots extending lengthwise at spaced locations on the body, and said means for carrying including a suture receiving opening extending through the tip.

11. The combination of claim 10 in which the bone anchor further includes at least one ridge extending outwardly from the exterior of the body and defining an edge adapted to lodge in the wall of the bore hole.

12. A method for anchoring a suture and suture anchor within a bone, wherein the suture anchor has a tip through which a hole is formed and through which hole the suture extends, the suture anchor also defining a barb that is adapted to engage the wall of the hole in the bone, comprising:

forming a hole in the bone;

selecting an inserter device having a shaft and a depth member mounted to the shaft, the shaft being selectively movable relative to the depth member;

positioning the suture anchor on the shaft;

inserting the suture anchor, carrying the suture through the hole in its tip, into the hole in the bone by moving the shaft into the hole; and limiting the depth of insertion of the anchor member by limiting the movement of the shaft by contacting the depth member against the bone.

* * * * *